(12) United States Patent
Riman et al.

(10) Patent No.: US 7,704,529 B2
(45) Date of Patent: Apr. 27, 2010

(54) MAGNESIUM-SUBSTITUTED HYDROXYAPATITES

(76) Inventors: Richard E Riman, 10 Monroe Ave., Belle Mead, NJ (US) 08502; Wojciech Suchanek, 240 Fox Hollow Dr., Apt 211, Cleveland, OH (US) 44124-6104; Pavel Shuk, 2762 Glenhaven Ave., # F, Copley, OH (US) 44321; Kevor S. TenHuisen, 40 Alexandria Way, Clinton, NJ (US) 08809; Chun-Wei Chen, 12 Sherry Rd., East Brunswick, NJ (US) 08816

( * ) Notice: Subject to any disclaimer, the term of this patent is extended or adjusted under 35 U.S.C. 154(b) by 657 days.

(21) Appl. No.: 11/089,745

(22) Filed: Mar. 25, 2005

(65) Prior Publication Data

US 2005/0186249 A1 Aug. 25, 2005

Related U.S. Application Data

(62) Division of application No. 09/800,127, filed on Mar. 6, 2001, now Pat. No. 6,921,544.

(51) Int. Cl.
*A61K 33/42* (2006.01)
(52) U.S. Cl. ............ 424/602; 423/201.1; 423/202.1; 424/422; 424/423; 424/604; 424/682; 523/113; 523/114; 523/115; 523/116; 623/16.11; 623/23.46; 623/23.51; 623/23.61; 623/23.62; 623/23.75
(58) Field of Classification Search .................. None
See application file for complete search history.

(56) References Cited

U.S. PATENT DOCUMENTS

| 4,097,935 A | 7/1978 | Jarcho | 3/1.9 |
| 5,830,480 A | 11/1998 | Ducheyne et al. | 424/450 |
| 6,027,742 A | 2/2000 | Lee et al. | 424/422 |

FOREIGN PATENT DOCUMENTS

| JP | 06245992 | 12/1994 |
| WO | 97/17285 | 5/1997 |
| WO | 99/32400 | 7/1999 |
| WO | WO00/03747 | 1/2000 |

OTHER PUBLICATIONS

Bertoni et al. "Nanocrystals of magnesium and fluoride substituted hydroxypatite" J. Inorg. Biochem., 72 (1):29-35 (1998).
Yasukawa et al. "Preparation—Mg CaHAP" J. Mater. Chem. 6(8) p. 1401-1405 (1996).
Bigi et al. "Magnesium Influence on Hydroxypatite Crystalization" J. Inor. Biochem. 49, 69-78 (1993).
Patel, P.N., "Magnesium Calcium Hydroxylapatite Solid Solutions", J. Inorg. Nucl. Chem, vol. 42, pp. 1129-1132 (1980).
Liao, J. et al., "Synthesis of Ca-Mg Apatite via a Mechanochemical Hydrothermal Process", J. Mater. Synth. Process, vol. 8, No. 5/6, pp. 305-311 (2000).
Yokogawa, Y. et al., "Synthesis of Calcium-Strontium, Calcium-Magnesium, Magnesium-Strontium Apatite Through Mechanochemical Method", Report of National Industrial Research Institute of Nagoya, vol. 45, No. 4, pp. 161-166 (1996).

*Primary Examiner*—Neil Levy
(74) *Attorney, Agent, or Firm*—Fox Rothschild LLP; Peter J. Butch, III

(57) ABSTRACT

A stable, phase-pure magnesium-substituted crystalline hydroxyapatite containing from about 2.0 to about 29 wt % magnesium, wherein at least 75 wt % of the magnesium content is substituted for calcium ions in the hydroxyapatite lattice structure.

9 Claims, No Drawings

MAGNESIUM-SUBSTITUTED HYDROXYAPATITES

CROSS REFERENCE TO RELATED APPLICATION

This application is a Divisional of U.S. patent application Ser. No. 09/800,127 (pending) which was filed on Mar. 6, 2001 with the U.S. Patent and Trademark Office, the disclosure of which is incorporated herein by reference.

BACKGROUND OF THE INVENTION

The present invention relates to methods for magnesium substitution of crystalline hydroxyapatites that provide heretofore unobtained levels of magnesium incorporation into the hydroxyapatite lattice structure. The present invention also relates to phase-pure magnesium-substituted crystalline hydroxyapatites obtained thereby.

Hydroxyapatite (HAp, chemical formula $Ca_{10}(PO_4)_6(OH)_2$) has attracted the attention of researchers over the past thirty years as an implant material because of its excellent biocompatibility and bioactivity. HAp has been extensively used in medicine for implant fabrication. It is commonly the material of choice for the fabrication of dense and porous bioceramics. Its general uses include biocompatible phase-reinforcement in composites, coatings on metal implants and granular fill for direct incorporation into human tissue. It has also been extensively investigated for non-medical applications such as a packing material/support for column chromatography, gas sensors and catalysts, as a host material for lasers, and as a plant growth substrate. All properties of HAp, including bioactivity, biocompatibility, solubility and adsorption properties can be tailored within a wide range by controlling qualitatively and quantitatively the ions substituted for $Ca^{2+}$, $PO_4^{3-}$ and $OH^-$ in the HAp lattice structure.

Magnesium has been known as one of the cationic substitutes for calcium in the HAp lattice structure. Magnesium-substituted HAp can be expressed by the simplified chemical formula:

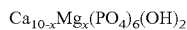

$$Ca_{10-x}Mg_x(PO_4)_6(OH)_2$$

with x/10 representing atom-percent substitution of magnesium ions for calcium ions.

Magnesium is also one of the predominant substitutes for calcium in biological apatites. Enamel, dentin, and bone contain respectively 0.44 wt %, 1.23 wt % and 0.72 wt % magnesium. Accordingly, magnesium-substituted HAp materials (Mg—HAp) are expected to have excellent biocompatibility and properties that can be favorably compared with those of hard tissue. U.S. Pat. No. 6,027,742 and WO 00/03747, for example, disclose the use of Mg—HAp as bone substitutes and for dental applications, respectively.

Increasing concentration of MG in HAp has the following effects on its properties: (a) gradual decrease in crystallinity, (b) increase $HPO_4$ incorporation, and (c) increase in extent of dissolution. Magnesium is closely associated with mineralization of calcified tissues, and indirectly influences mineral metabolism. It has been suggested that magnesium directly stimulates osteoblast proliferation with an effect comparable to that of insulin (a known growth factor for osteoblast). Thus, it becomes possible to tailor the physicochemical properties of HAp, as well as its biocompatibility and bioactivity, by controlling the Mg substitution of the HAp lattice structure.

Because the optimum amounts of magnesium in artificial HAp ceramics can vary with different applications, the capability to control precisely the amounts of magnesium in HAp in the widest possible range by controlling the synthesis procedure is of primary importance. Mg—HAp powders have been prepared by precipitation and hydrolysis methods with the replacement of calcium by magnesium limited to no more than 0.3 wt %.

Bigi et al., *J. Inorg. Biochem*, 49, 69-78(1993) disclosed the synthesis of crystalline Mg—HAp powders with up to about 30 atom-percent (about 7.5 wt %) of magnesium under hydrothermal conditions at 120° C. Above this level of magnesium substitution the product was reported to be completely amorphous. At most, 7 atom-percent (about 1.7 wt %) of magnesium ions were reported to be capable of substitution for calcium in the HAp lattice structure.

A need exists for crystalline Mg—HAp powders with a higher magnesium content, a higher degree of magnesium-substitution in the HAp lattice structure, as well as a simple and inexpensive synthesis of Mg—HAp.

SUMMARY OF THE INVENTION

This need is met by the present invention. It has now been discovered that hybrid mechanochemical-hydrothermal synthesis techniques may be employed to produce magnesium-substituted HAp with not only heretofore unobtained magnesium levels, but also with levels of magnesium incorporation into the HAp lattice structure that was not believed possible until now.

Mechanochemical powder synthesis is a solid-state synthesis method that takes advantage of the perturbation of surface-bonded species by pressure to enhance thermodynamic and kinetic reactions between solids. Pressure can be applied at room temperature by milling equipment ranging from low-energy ball mills to high-energy stirred mills. The main advantages of the mechanochemical synthesis of ceramic powders are simplicity and low cost. Therefore, a variety of chemical compounds have been already prepared by this technique, for example $CaSiO_3$, $PbTiO_3$, and $0.9Pb(Mg_{1/3}Nb_{2/3})O_3$-$0.1PbTiO_3$, etc. Since the mechanochemical synthesis involves only solid-state reactions, it is clearly distinguished from the mechanochemical-hydrothermal synthesis (sometimes called "wet" mechanochemical), which takes advantage of the presence of an aqueous solution in the system. An aqueous solution can actively participate in the mechanochemical reaction by acceleration of dissolution, diffusion, adsorption, reaction rate and crystallization (nucleation and growth). The mechanochemical activation of slurries can generate local zones of high temperatures (up to 450-700° C.) and high pressure due to friction effects and adiabatic heating of gas bubbles (if present in the slurry), while the overall temperature is close to the room temperature.

The mechanochemical-hydrothermal technique is thus located at the intersection of hydrothermal and mechanochemical processing. The mechanochemical-hydrothermal route produces comparable amounts of HAp powder as the hydrothermal processing but it requires lower temperature, i.e., room temperature, as compared to typically 90-200° C. for the hydrothermal processing. Perhaps the biggest advantage of the room-temperature mechanochemical-hydrothermal processing is that there is no need for a pressure vessel and no need to heat the reaction mixture. The reaction is thus conducted either as a comminuting or stirred tank reaction process.

Therefore, according to one aspect of the present invention, a stable, phase-pure magnesium-substituted crystalline hydroxyapatite is provided containing from about 2.0 to about 29 wt % magnesium, wherein at least 75 wt % of the magnesium content is substituted for calcium ions in the hydroxyapatite lattice structure. The Mg—HAp of the present invention forms as crystal agglomerates. The present invention therefore also includes particles of the Mg—HAp of the present invention having a particle size between about 5 mm and about 100 microns.

The high magnesium content and high degree of magnesium substitution in the HAp lattice structure is attributable to the combined use of mechanochemical and hydrothermal process steps. Therefore, according to another aspect of the present invention, a method for the preparation of Mg—HAp is provided, which includes the step of mechanochemically reacting in a stoichiometric ratio selected to provide a predetermined level of magnesium substitution, a source of calcium ions, a source of magnesium ions, a source of phosphate ions and a source of hydroxide ions, at least one of which is soluble in water, in an aqueous reaction medium until Mg—HAp is formed. One material may serve as a multiple ion source. For example, magnesium hydroxide may be employed as a source of both magnesium and hydroxide ions, or calcium hydrogen phosphate may be employed as a source of calcium and phosphate ions.

The preferred source of phosphate ions is diammonium hydrogen phosphate, which is highly water soluble. Hydroxides of calcium and magnesium are preferred sources of these two cations. With magnesium hydroxide, at higher levels of magnesium substitution, unreacted magnesium hydroxide should be removed, preferably by washing the Mg—HAp in ammonium citrate aqueous solution so that the unreacted magnesium hydroxide preferentially dissolves therein.

The ammonium citrate washing step represents a novel approach to increasing the level of hydroxyapatite lattice-incorporated magnesium relative to the total magnesium content, as well as relative to the lattice-incorporated calcium. Therefore, according to another aspect of the present invention, a method is provided for increasing the magnesium content in the lattice structure of magnesium-substituted crystalline hydroxyapatite relative to the calcium content of the lattice structure and to the non-lattice magnesium content, in which the magnesium-substituted hydroxyapatite is washed with an aqueous ammonium citrate solution.

The Mg—HAp of the present invention more closely resembles biological apatites than conventional HAp ceramics. Therefore, according to another aspect of the present invention there is provided a biocompatible hard tissue implant containing the Mg—HAp of the present invention. For example, metal or polymeric hard tissue implants may be created that are coated with the Mg—HAp of the present invention, as well as implants that are formed from metal or polymeric Mg—HAp composite materials. The present invention also includes a granular fill for direct incorporation into human or animal tissues containing the Mg—HAp of the present invention, as well as dentifrice compositions, such as toothpaste, metal or polymeric composites for filling dental cavities, and bone cements containing the Mg—HAp of the present invention.

The easy to control stoichiometry makes the Mg—HAp of the present invention ideal for use as a packing material for chromatography columns and gas sensors, as well as a support for catalytic materials or a plant growth substrate. Stoichiometric optimization can provide the end use properties needed for each end-use application.

Therefore, accordingly to another aspect of the present invention, there is provided a packing material for use in a chromatography column or gas sensor, or as a support for a catalytic material, containing the Mg—HAp of the present invention. The present invention also provides host materials for luminescent applications containing the Mg—HAp of the present invention, as well as plant growth substrates containing the Mg—HAp of the present invention.

The present invention thus provides a means by which levels of magnesium substitution in HAp may be controlled by changing the ratio of calcium and magnesium ions in the source materials to tailor the end-product to specific end-use applications. The foregoing and other objects, features, and advantages of the present invention are more readily apparent from the detailed description of the preferred embodiments set forth below.

DETAILED DESCRIPTION OF THE PREFERRED EMBODIMENTS

The magnesium-substituted hydroxyapatites of the present invention are prepared by a combined mechanochemical-hydrothermal process. A source of magnesium ions, a source of calcium ions, a source of phosphate ions and a source of hydroxide ions are mechanochemically reacted in an aqueous reaction medium. At least one ion source is water-soluble.

For purposes of the present invention, "water-soluble" ion sources are defined as being materials having a solubility in water of at least about 2.0 g/L. A solubility greater than about 20 g/L is preferred.

Examples of magnesium ion sources include magnesium hydroxide, magnesium carbonate, magnesium acetate, magnesium halides, magnesium oxide, magnesium nitrate, magnesium phosphate, and the like. Magnesium hydroxide is preferred. Similarly, examples of calcium ion sources include calcium hydroxide, calcium carbonate, calcium acetate, calcium halides, calcium oxide, calcium nitrate, calcium phosphate, and the like. Calcium hydroxide is preferred.

Examples of phosphate ion sources include ammonium phosphates, calcium phosphates, magnesium phosphates, Group I phosphates such as potassium and sodium phosphates, and the like. A water-soluble phosphate ion source is preferred, with diammonium hydrogen phosphate being particularly preferred.

Hydroxide ion sources include hydroxide-containing compounds such as ammonium hydroxide, calcium hydroxide, magnesium hydroxide, sodium hydroxide, potassium hydroxide, and the like, and compounds that generate hydroxide ion in aqueous solution, such as ammonia, calcium oxide, magnesium oxide, and the like.

Depending upon the end-use application, other ion sources may be included as well, of a quality and quantity that do not disrupt the hydroxyapatite lattice structure. Thus, quantities of source materials may be employed that introduce up to about 25 wt % into the Mg—HAp lattice structure, depending upon the ions, of one or more cations, for example, sodium, lithium, barium, strontium, zinc, cadmium, lead, vanadium, silicon, germanium, iron, arsenic, manganese, aluminum, rare earth elements, cobalt, silver, chromium, antimony, and the like, or one or more anions, for example, carbonate, halides, oxygen, sulfur and the like. Suitable additional ion sources and appropriate quantities thereof are readily determined by those of ordinary skill in the art without undue experimentation.

Preferably, at least one ion source is water-insoluble or reacts to form an insoluble apatite phase precursor. This provides a substrate medium for the application of mechanochemical force at the same time that the hydrothermal process steps are being carried out.

Stoichiometric quantities of the ion sources are employed, selected to provide the desired ratio of individual HAp lattice components, especially the ratio of calcium to magnesium and the ration cations occupying the calcium sites to phosphorous. Water-soluble ion sources are dissolved in the aqueous reaction medium, with a slurry being formed of the non-water-soluble ion sources. The preferred aqueous medium is essentially pure distilled water, that more preferably has been deionized and/or demineralized. Up to about 40 wt % of the combined amounts of the ion sources may be added to the aqueous reaction medium, at a temperature maintained between about 8 and 35° C., and preferably between about 25 and about 35° C., until Mg—HAp is formed. External sources of heat are not needed, with sufficient heat being supplied by milling friction. Instead, external cooling may be needed because the molecular activation of the slurry can generate local zones of high temperature (up to 450-700° C.) and corresponding pressures due to friction and adiabatic heating of gas bubbles.

With stirring of the aqueous slurry/solution, the ion sources are mechanochemically reacted, typically by the application of physical force to the water-insoluble ion sources or insoluble apatite precursors that are suspended as a slurry in the aqueous reaction medium containing the water-soluble ion sources. Preferred mechanochemical reaction processes comminute the ion source slurry particles, preferably by milling or grinding the water insoluble ion source particles with heating of the aqueous reaction medium into which the water-soluble ion source has been dissolved. Preferred methods at the same time frictionally heat the aqueous reaction medium/slurry while the slurry particles are being milled or ground, so that the mechanochemical and hydrothermal process step are performed simultaneously.

Multi-ring media mills are preferred. The grinding mechanism consists of a central rotating stainless steel shaft, which drives a plurality of stainless steel sub-shafts (sleeve-lined with zirconia-toughened alumina) that are connected symmetrically to the central shaft. Each sub-shaft contains a plurality of stacked zirconia rings, which rotate eccentrically around each sub-shaft. When the central shaft is rotating, the zirconia rings on the sub-shafts are moved by the centrifugal force radially outwards, applying force on the inner wall of the milling vessel, which is ceramic lined. Solid slurry particles located between the rotating rings and the liner wall are consequently comminuted.

The comminuting step is performed at rotation speeds between 800 and 1500 r.p.m. (for the multi-ring media mill), or higher for higher solid content slurries for at least 1 hour, and preferably from between about 1 and about 10 hours, with the temperature of the aqueous slurry maintained between about 25 and about 35° C. for the duration. The solid phase is then recovered and washed with distilled water, preferably repeatedly. The solid phase is then once again isolated and excess water is removed, preferably by first centrifuging the material followed by oven drying at a temperature between about 40 and 200° C. Lyophilization may also be employed to remove excess water. If desired, dry grinding may be performed to reduce the powder particle size.

The inventive method advantageously employs environmentally benign ion sources in an aqueous reaction medium at mild temperatures. The elevated temperatures associated with prior art calcination processes are thereby avoided.

When all of the ion sources are water-soluble a solution-phase reaction is first performed, followed by heating to drive off the aqueous phase to recover a powder material that is milled while wet through to dryness to complete the mechanochemical reaction. However, a slurry-based reaction is preferred in which one of the ion sources is water-insoluble. Or two water-soluble material may be employed that form an insoluble apatite precursor that is then milled while wet through to dryness to complete the mechanochemical reaction. Under certain circumstances understood by those skilled in the art, Mg—HAp's of present invention may be produced solely by dry milling.

With water-insoluble magnesium ion sources, such as magnesium hydroxide, magnesium oxide, magnesium phosphates, and the like, for higher levels of magnesium substitution, unreacted quantities of the magnesium ion source will remain that have to be removed by selective washing of the Mg—HAp. In a particularly preferred embodiment, the Mg—HAp is washed with ammonium citrate aqueous solution, into which the unreacted magnesium ion source will preferentially dissolve. After this washing step, the purified Mg—HAp is washed, preferably repeatedly, with distilled water and then dried.

In a preferred procedure Mg—HAp powders are prepared by suspending a mixture of calcium hydroxide and magnesium hydroxide powders in water and subsequently adding a soluble diammonium hydrogen phosphate powder, quantities as required by stoichiometry. The mechanochemical-hydrothermal synthesis is then performed by placing the slurry into a multi-ring media mill and then grinding the slurry. The resulting powder is washed using water to remove soluble salts with an ammonium citrate aqueous solution washing step performed first for reactions employing higher levels of magnesium substitution. Following the water washing, the Mg—HAp is then dried.

The inventive method provides crystalline Mg—HAp powders in which at least 75 wt % of the magnesium content is substituted for calcium ions in the hydroxyapatite lattice structure. Crystalline Mg—HAp in which essentially all of the magnesium content is substituted for calcium ions in the hydroxyapatite lattice structure can be readily obtained without undue effort. Accordingly, substitution levels between about 80 wt % and 98 wt % can be readily obtained by the ordinarily skilled artisan following the teachings of the present specification.

The crystalline Mg—HAp will have a magnesium content between about 2.0 and about 29 wt %, with levels between about 3.5 and about 28.4 wt % being preferred. Levels between about 5 and about 25 wt % are even more preferred, with a level of at least 10 wt % being most preferred. The crystalline Mg—HAp of the present invention forms crystals agglomerates having an approximate particles ranging in size between about 5 nm and about 10 microns.

The crystalline Mg—HAp of the present invention is useful in the preparation of compounds for use as granular fill for direct incorporation into the hard tissues of humans or other animals, and as bone implantable materials. The present invention thus includes granular fill compounds, bone implant materials, tooth filling compounds, bone cements and dentifrices containing the Mg—HAp of the present invention. The products are formulated and prepared by substituting the Mg—HAp of the present invention for HAp in conventional HAp-based products. The compounds may be prepared from metallic and polymeric Mg—HAp composites.

The Mg—HAp of the present invention may also be substituted for the HAp in support materials for gas sensors and chromatography columns. It may also be substituted for HAp and other support substrates and hosts in catalytic supports, plant growth substrates and in host materials for luminescent applications. Therefore, the present invention also includes packing materials for chromatography columns and gas sensors, catalytic supports, plant growth substrates and host materials for luminescent applications containing the Mg—HAp of the present invention.

The following non-limiting examples set forth herein below illustrates certain aspects of the invention. All parts and percentages are by weight unless otherwise noted and all temperatures are in degrees Celsius. Stoichiometric values in HAp and Mg—HAp formulas are approximate.

EXAMPLES

Example 1

Mechanochemical-Hydrothermal Synthesis of $Ca_8Mg_2(PO_4)_6(OH)_2$

Calcium hydroxide, magnesium hydroxide and solid diammonium hydrogen phosphate (analytical grade, Alfa Aesar, Ward Hill, Mass.) were used as reactants for the synthesis of Mg—HAp. First, a suspension containing a powder mixture of 22.170 g calcium hydroxide and 4.557 g magnesium hydroxide in 350 mL deionized water was prepared inside a 500 ml glass beaker. Subsequently, 29.410 g of diammonium hydrogen phosphate powder was slowly added to the same beaker at constant vigorous stirring using a magnetic stirrer for about 10 minutes. The (Ca+Mg)P molar ratio in the starting slurry was 1.67. The presence of water adsorbed on all reactants was measured by thermogravimetry to maintain the targeted stoichiometry. The pH of the slurry was about 10.3, measured using a glass electrode connected to a small pH-meter (ACCUMET™ Model 805 MP, Fisher Scientific, Pittsburgh, Pa.) and calibrated with respect to a buffer solution (pH=10.00, Fisher Scientific). The mechanochemical-hydrothermal synthesis was performed by placing the slurry into a laboratory scale mill (Model MIC-0, NARA Machinery Co., Tokyo, Japan) equipped with a zirconia liner and a zirconia ring grinding media. Grinding of the slurry was carried out in air, initially at a rotation speed of 1500 rpm for one hour and then at 800 rpm for four hours. Temperature during the grinding was measured using a thermocouple and determined to be 33° C. at 1500 rpm and 28° C. at 800 rpm.

Washing of the solid phase after the mechanochemical-hydrothermal synthesis was accomplished by four cycles of shaking the solid with distilled water in 250 mL HDPE bottles using a hand shaker machine Model M37615, Barnstead/Thermolyne, Dubuque, Iowa) followed by centrifuging at 4500 rpm for 30 minutes (Induction Drive Centrifuge, Model J2-21M, Beckman Instruments, Fullerton, Calif.). The washed solid phase was dried in an oven at 70° C. for 24 hours (ISOTEMP™ Oven, Model 230G Fisher Scientific) and ground into powder.

The synthesized Mg—HAp powder contained a fraction of unreacted magnesium hydroxide. Therefore, it was suspended in a 0.2 M ammonium citrate aqueous solution. The ammonium citrate solution was prepared in a 200 mL glass beaker by dissolving 3.843 g of solid citric acid (reagent grade, Aldrich, Milwaukee, Wis.) in 100 mL of distilled water and subsequently slowly adding ammonia solution (reagent grade, Fisher Scientific) to yield a pH between 8 and 10. 1.0 g of the Mg—HAp containing unreacted magnesium hydroxide was then suspended in the solution. The dissolution of the magnesium hydroxide was accomplished under a vigorous stirring using a magnetic stirrer for 12 hours, after which the prior distilled water washing, centrifuging and drying steps were repeated.

Phase pure crystalline Mg—HAp essentially free of unreacted magnesium hydroxide and having a magnesium content of approximately 10 wt % in which essentially all of the magnesium content was substituted for calcium ions in the hydroxyapatite lattice structure was confirmed by x-ray defraction, Fourier Transform Infra-Red spectroscopy, thermogravimetric analysis and chemical analysis.

Dynamic light scattering revealed the particle size distribution of the Mg—HAp to be between about 130 and about 2100 nm with a specific surface area of about 129 m²/g, indicating agglomeration. Scanning Electron Microscopy confirmed agglomerates of nanosized Mg—HAp crystals.

Example 2

Mechanochemical-Hydrothermal Synthesis of $Ca_7Mg_3(PO_4)_6(OH)_2$

Ca(OH), MG(OH)$_2$ and solid (NH$_4$)$_2$HPO$_4$ (analytical grade, Alfa Aesar, Ward Hill, Mass.) were used as reactants for the synthesis of Mg—HAp. First, a suspension containing a powdered mixture of 19.150 g Ca(OH)$_2$ and 6.717 g Mg(OH)$_2$ in 350 mL of deionized water was prepared inside a 500 mL glass beaker. Subsequently, 29.028 g of (NH$_4$)$_2$HPO$_4$ powder was slowly added to the same beaker at constant vigorous stirring using a magnetic stirrer for about 10 min. The (Ca+Mg)/P molar ratio in the starting slurry was 1.67. The presence of water adsorbed on all reactants was measured by thermogravimetry to maintain the targeted stoichiometries. The pH of the slurry was about 10.2, measured using a glass electrode connected to a pH-meter (Accumet Model 805 MP, Fisher Scientific, Pittsburgh, Pa.) and calibrated with respect to a buffer solution (pH=10.00, Fisher Scientific).

The mechanochemical-hydrothermal synthesis was performed by placing the slurry into a laboratory-scale mill (model MIC-0, NARA Machinery Co., Tokyo, Japan) equipped with a zirconia liner and zirconia ring grinding media. Grinding of the slurry was carried out in air, initially at a rotation speed of 1500 rpm for 1 h and then at 800 rpm for 4 h. Temperature during the grinding was measured using a thermocouple and was determined to be 33° C. at 1500 rpm and 28° C. at 800 rpm. Washing of the solid phase after the mechanochemical-hydrothermal synthesis was accomplished by 2-6 cycles of shaking the solid with distilled water in 2-6 HDPE 250 mL bottles using a hand shaker machine (Model M37615, Barnstead/Thermolyne, Dubuque, Iowa) followed by centrifuging at 4500 rpm for 30 min. (Induction Drive Centrifuge, Model J2-21M, Beckman Instruments, Fullerton Calif.).

The washed solid phase was dried in an oven at 70° C. for 24 h (Isotemp oven, model 230G, Fisher Scientific) and ground into powder. The synthesized MG-HAp powder contained a fraction of unreacted Mg(OH)2. Therefore, it was suspended in 0.2 M-ammonium citrate aqueous solution. The ammonium citrate solution was prepared in a 250 mL glass beaker by dissolving 3.843 g of solid citric acid (reagent grade, Aldrich, Milwaukee, Wis.) in 200 mL of distilled water and subsequently slowly adding ammonia solution (reagent grade, Fisher Scientific) to yield a pH of 10. 1.0 g of the Mg—HAp containing unreached Mg(OH)$_2$ was then suspended in the solution. The dissolution of the Mg(OH)$_2$ was accomplished under a vigorous stirring using a magnetic stirrer for 24 h. This procedure was repeated once under the same conditions, in order to completely remove the Mg(OH)$_2$ phase.

Properties: Mg content: 15 wt %, particle size distribution: 250-4500 nm, SSA: 115 m²/g.

Comparative Example

Example 1 was repeated substituting 2-propanol ($C_3H_7OH$, histological grade, Fisher Scientific) for water, so that the reaction conditions were purely mechanochemical. Under otherwise equivalent conditions, no Mg—HAp was observed to form. This emphasizes the importance of the hydrothermal conditions provided by the aqueous reaction medium in which at least one of the ion sources is soluble, and which thus actively participates in the synthesis reaction by dissolving one of the reactants.

The present invention thus provides for the reproducible and low-cost fabrication of high-quality Mg—HAp powders in large batch sizes. The foregoing examples and description of the preferred embodiment should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and scope of the invention, and all such variations are intended to be included within the scope of the following claims.

What is claimed is:

1. A stable, phase-pure magnesium-substituted crystalline hydroxyapatite comprising from about 10 wt % to about 29 wt % magnesium, wherein at least 80 wt % of the magnesium content of said magnesium-substituted hydroxyapatite is substituted for calcium ions in the hydroxyapatite lattice structure, wherein said magnesium-substituted hydroxyapatite is made by a process comprising the step of mechanochemically comminuting and dissolving while hydrothermally reacting without external heating a source of calcium ions, a source of magnesium ions, a source of phosphate ions and a source of hydroxide ions, at least one of which is soluble in water, in a aqueous reaction medium until said magnesium substituted-hydroxyapatite is formed, wherein at least one of said source of calcium ions, source of magnesium ions, source of phosphate ions and source of hydroxide ions is water-insoluble or forms a water-insoluble apatite precursor.

2. The phase-pure magnesium-substituted crystalline hydroxyapatite of claim 1, wherein essentially all of the magnesium content is substituted for calcium ions in the hydroxyapatite lattice structure.

3. The phase-pure magnesium-substituted crystalline hydroxyapatite of claim 1, comprising crystal agglomerates having a particle size between about 5 nm and about 100 microns.

4. A biocompatible hard tissue implant comprising the magnesium-substituted hydroxyapatite of claim 1.

5. The biocompatible hard tissue implant of claim 4, comprising a metal or polymeric implant coated with said magnesium-substituted hydroxyapatite.

6. The biocompatible hard tissue implant of claim 4, comprising a polymeric composite.

7. A granular fill for direct incorporation into human or animal tissues comprising the magnesium-substituted hydroxyapatite of claim 1.

8. The granular fill of claim 7, comprising a metal or polymeric composite for filling dental cavities.

9. A dentifrice composition comprising the magnesium-substituted hydroxyapatite of claim 1.

* * * * *